United States Patent [19]

Kawai et al.

[11] Patent Number: 5,684,210
[45] Date of Patent: Nov. 4, 1997

[54] METHOD OF PURIFYING FLUOROMETHYL-1,1,1,3,3,3, HEXAFLUOROISOPROPYL ETHER

[75] Inventors: Toshikazu Kawai; Takaaki Yoshimura; Mineo Watanabe; Manami Kumakura, all of Kawagoe, Japan

[73] Assignee: Central Glass Company, Limited, Yamaguchi, Japan

[21] Appl. No.: 545,715

[22] PCT Filed: Mar. 23, 1995

[86] PCT No.: PCT/JP95/00536

§ 371 Date: Nov. 7, 1995

§ 102(e) Date: Nov. 7, 1995

[87] PCT Pub. No.: WO95/26326

PCT Pub. Date: Oct. 5, 1995

[30] Foreign Application Priority Data

Mar. 28, 1994 [JP] Japan ......................... 6-57305

[51] Int. Cl.$^6$ ..................................... C07C 41/00

[52] U.S. Cl. ............................... 568/682; 568/683
[58] Field of Search ........................ 568/682, 683

[56] References Cited

U.S. PATENT DOCUMENTS 4,250,334  2/1981  Coon et al. .
4,328,376  5/1982  Berger et al. .

FOREIGN PATENT DOCUMENTS

WO93/12057  6/1993  WIPO .

*Primary Examiner*—José G. Dees
*Assistant Examiner*—Karl J. Puttlitz, Jr.
*Attorney, Agent, or Firm*—Keck, Mahin & Cate

[57] ABSTRACT

It is possible to obtain fluoromethyl-1,1,1,3,3,3-hexafluoroisopropyl ether which has a high purity and in which an impurity making the purification by distillation difficult has been removed, by contacting a crude fluoromethyl-1,1,1,3,3,3-hexafluoroisopropyl ether with a Brönsted acid(s), a Lewis acid(s) or an acid(s) fixed to a resin or the like.

5 Claims, No Drawings

METHOD OF PURIFYING FLUOROMETHYL-1,1,1,3,3,3, HEXAFLUOROISOPROPYL ETHER

TECHNOLOGICAL FIELD

The present invention relates to a method of purifying fluoromethyl-1,1,1,3,3,3-hexafluoroisopropyl ether, which is widely used as a pharmaceutical and particularly as an inhalation anesthetic.

BACKGROUND TECHNOLOGY

Hitherto, fluoromethyl-1,1,1,3,3,3-hexafluoroisopropyl ether has been widely used as an inhalation anesthetic which is safe for use. For example, the production method is described in detail in U.S. Pat. No. 4,250,334, while the purifying method for obtaining a purity suitable for medical use is described in U.S. Pat. No. 4,328,376. To be concrete, according to the production method described in U.S. Pat. No. 4,250,334, when concentrated sulfuric acid and hydrogen fluoride are added to paraformaldehyde, and then when a gas generated by a method in which 1,1',1,3,3,3-hexafluoroisopropyl alcohol is added dropwise to this heated reaction mixture is collected, the non-reacted alcohol and organic by-products such as formal, acetal and the like, which have been formed as by-products, are recovered along with the aimed product. However, according to the description of U.S. Pat. No. 4,328,376, it has been found that fluoromethyl-1,1,1,3,3,3-hexafluoroisopropyl ether synthesized by such method contains a small amount of an olefin compound in addition to the above-mentioned by-products. In view of that this compound shows an azeotropic behavior in distillation and thus the purification does not succeed by a distillation means, it has succeeded in obtaining fluoromethyl-1,1,1,3,3,3-hexafluoroisopropyl ether, which has a high purity, by chemically treating the obtained crude fluoromethylhexafluoroisopropyl ether with an amine or the like, and then by subjecting it to a distillation process. Fluoromethylhexafluoroisopropyl ether obtained by using the purification method, in which the amine or the like is used, is satisfactory in increasing the purity, but a small amount of the amine or the like remains instead in fluoromethyl-1,1,1,3,3,3-hexafluoroisopropyl ether, resulting in a fault accompanied by a secondary effect of the recognizable smell of the amine, which is extremely undesirable as an inhalation anesthetic.

In use of the aimed inhalation anesthetic in the present invention, there is no doubt but that it is demanded that an undesirable impurity is essentially not contained. In order to achieve this aim, a method of improving the purity of fluoromethyl-1,1,1,3,3,3-hexafluoroisopropyl ether was eagerly continuously examined. As a result, when fluoromethyl-1,1,1,3,3,3-hexafluoroisopropyl ether is produced from 1,1,1,3,3,3-hexafluoroisopropyl alcohol, hydrogen fluoride, concentrated sulfuric acid and formaldehyde, in accordance with the method described in U.S. Pat. No. 4,250,334, it was found that a fluorinated ether(s) except fluoromethyl-1,1,1,3,3,3-hexafluoroisopropyl ether (referred to as "fluorinated ether as a by-product" in the present specification) or the like and a high-boiling-point polyether(s) or the like are inevitably produced, as well as the by-products such as formal, acetal and the like, which are described in the above-mentioned patent specification, and that, of these, particularly the fluorinated ether as a by-product or the like suppresses the purity increase of fluoromethyl-1,1,1,3,3,3-hexafluoroisopropyl ether. With regard to most of these by-products, it is usual that they receive the chemical or physical action and thus essentially do not remain in the product, by conducting the recovery treatment method, i.e. water washing, alkali washing, drying, distillation or the like, which is usually used against such reaction product. There has been found an unexpected property troublesome in the purification treatment, in which, although among the fluorinated ethers as by-products or the like, bisfluoromethyl ether alone is an extremely unstable compound, when it coexists with fluoromethyl-1,1,1,3,3,3-hexafluoro-isopropyl ether, it is not separated by a usual recovery treatment method, i.e. water washing, alkali washing, drying or the like. Thus, when the purification by distillation of fluoromethyl-1,1,1,3,3,3-hexafluoroisopropyl ether containing bisfluoromethyl ether was tried, contrary to the expectation, it was confirmed that bisfluoromethyl ether and fluoromethyl-1,1,1,3,3,3-hexafluoroisopropyl ether do not easily separate from each other and show an azeotropic behavior, resulting in a failure of the recovery of the product to have a sufficiently high purity. Therefore, it is clear that the establishment of a method for efficiently removing this bisfluoromethyl ether is an essential subject for improving the purity of fluoromethyl-1,1,1,3,3,3-hexafluoroisopropyl ether.

DISCLOSURE OF THE INVENTION

In view of such problem of prior art, the present inventors have eagerly examined a purification method for obtaining fluoromethyl-1,1,1,3,3,3-hexafluoroisopropyl ether essentially not containing bisfluoromethyl ether, without having a bad influence on a useful fluoromethyl-1,1,1,3,3,3-hexafluoroisopropyl ether. As a result, we have found that, if the fluorinated ether formed as a by-product in the synthesis of fluoromethyl-1,1,1,3,3,3-hexafluoroisopropyl ether is contacted with a Brösted acid(s), and/or a Lewis acid(s), and/or an acid(s) fixed to a resin or the like, it is efficiently removed. Thus, we have achieved the present invention. In other words, the present invention provides a method of purifying fluoromethyl-1,1,1,3,3,3-hexafluoroisopropyl ether, characterized in that a fluorinated ether formed as a by-product in the synthesis of fluoromethyl-1,1,1,3,3,3-hexafluoroisopropyl ether is removed by contact with a Brösted acid(s), and/or a Lewis acid(s), and/or an acid(s) fixed to a resin or the like, followed by a treatment with an alkaline aqueous solution.

It is possible to obtain fluoromethyl-1,1,1,3,3,3-hexafluoroisopropyl ether having a high purity and no bad-smell, by separating through distillation a polyether(s) or the like having a higher boiling point than that of fluoromethylhexafluoroisopropyl ether from a crude product of fluoromethyl-1,1,1,3,3,3-hexafluoroisopropyl ether obtained by the purifying method of the present invention.

In the present invention, there are shown, as examples of Brösted acid used for removing the fluorinated ether, sulfuric acid, fuming sulfuric acid, sulfuric acid anhydride, hydrogen bromide, hydrogen iodide, trifluoroacetic acid and trifluoromethanesulfonic acid, and, as examples of Lewis acid, trifluoroboron, tetrafluorotitanium and the like. In some cases, it is possible to use these under a condition of aqueous solution or the like. Furthermore, the acid(s) fixed to a resin or the like is referred to as one present as a solid upon the treatment operation and as a resin having a sulfonic acid group, phosphoric acid group or the like. It is possible to cite as this a so-called cation-type ion-exchange resin and the like. In particular, Nafion Resin (the product of DuPont Co.) and the like are suitable for use. In the present invention, in connection with a manner to use a Brösted acid(s), and/or a Lewis acid(s), and/or an acid(s) fixed to a resin or the like (in the following, abbreviated to "the acid(s) or the like"), it is possible to take a combination that a person skilled in the art can easily think of in using these acids or the like. That is, it is not precluded to use one selected from or a combination of at least two selected from these acids or the like.

With respect to the amount of these acids or the like for use, in case of a Brönsted acid(s) and/or a Lewis acid(s), the molar ratio of the acid(s) or the like to the fluorinated ether as a by-product is from 0.2 to 20 and preferably from 1 to 10. If the molar ratio of the acid(s) or the like to the fluorinated ether as a by-product is not higher than 0.2, it is not preferable because the complete removal of the fluorinated ether as a by-product is impossible. Although the excessive use is not particularly limited, it is preferable to use a small amount for facilitating the separation operation and the alkali washing, after the treatment with the acid(s) or the like. Thus, the molar ratio of the acid(s) or the like to the fluorinated ether as a by-product is not higher than 20, and not higher than 10 is preferably used. Furthermore, in case of the acid(s) fixed to a resin or the like, the weight ratio of the acid(s) fixed to a resin or the like to crude fluoromethyl-1,1,1,3,3,3-hexafluoroisopropyl ether is preferably from 0.01 to 0.5 because the solid-liquid reaction makes the treatment rate sufficient. If it is not higher than 0.01, the treatment takes a long time. If it is not lower than 0.5, there is not a technical disadvantage in particular. However, this not economically preferable. The treatment temperature with the acid(s) or the like is from 0° to 100° C., preferably from 10° to 60° C. and more preferably from 20° to 40° C. If it is not higher than 0° C., the treatment takes a long time. If it exceeds 100° C., the decomposition of a small amount of fluoromethyl-1,1,1,3,3,3-hexafluoroisopropyl ether will be undesirably caused. In case that the treatment is conducted in the vicinity of normal pressure, it is most preferable to conduct the treatment at about the atmospheric temperature from 20° to 40° C., in view of the matter of equipment and that the above-mentioned decomposition is not caused. The treatment pressure may be an arbitrary pressure because it does not have a particular effect on the treatment result. The treatment is usually conducted at a pressure from 1 to 10 kg/cm$^2$.

THE BEST MODE TO CARRY OUT THE INVENTION

Hereinafter, the present invention will be clearly described with reference to Examples, but the present invention is not limited to Examples. The analysis was conducted by gas chromatography. In Examples, all of "%" refer to weight %.

EXAMPLE 1

A 500 ml reaction vessel was charged with 50 ml of 98% sulfuric acid, 100 g (5 mol) of hydrogen fluoride, and 30 g (1 mol) of paraformaldehyde. This reaction mixture was heated to 65° C. Then, 134 g (0.8 mol) of 1,1,1,3,3,3-hexafluoroisopropyl alcohol was added on a dropwise basis, over 2 hr. Vapors generated by the reaction were collected using water. With this, 140 g of crude fluoromethyl-1,1,1,3,3,3-hexafluoroisopropyl ether was obtained. This crude fluoromethyl-1,1,1,3,3,3-hexafluoroisopropyl ether contained 1.3% of bisfluoromethyl ether. It contained 10.6% of a polyether(s) or the like.

A 50 ml reaction vessel was charged with 25 g of this crude fluoromethyl-1,1,1,3,3,3-hexafluoroisopropyl ether, followed by the addition of 1.3 g (three times bisfluoromethyl ether by mol) of 80% sulfuric acid. Then, stirring was conducted for 4 hr at 35° C. With this, bisfluoromethyl ether was decreased to 0.01%.

Then, it was washed with 5 g of 10% NaOH aqueous solution and then with 10 g of water, followed by distillation. With this, 18.9 g of fluoromethyl-1,1,1,3,3,3-hexafluoroisopropyl ether having a purity of 99.99% was obtained.

EXAMPLE 2

A 50 ml reaction vessel was charged with 25 g of crude fluoromethyl-1,1,1,3,3,3-hexafluoroisopropyl ether containing 1.3% of bisfluoromethyl ether and 12.3% of a polyether (s) or the like, which had been obtained in EXAMPLE 1. Then, 1.4 g (three times bisfluoromethyl ether by mol) of tetrafluorotitanium was added. Then, stirring was conducted for 4 hr at 35° C. With this, bisfluoromethyl ether decreased to 0.003%.

Then, it was washed with 5 g of 10% NaOH aqueous solution and then with 10 g of water, followed by distillation. With this, 19.0 g of fluoromethyl-1,1,1,3,3,3-hexafluoroisopropyl ether having a purity of 99.99% was obtained.

EXAMPLE 3

A 50 ml reaction vessel was charged with 25 g of crude fluoromethyl-1,1,1,3,3,3-hexafluoroisopropyl ether containing 1.3% of bisfluoromethyl ether and 12.3% of a polyether (s) or the like, which had been obtained in EXAMPLE 1. Then, 0.3 g (1.5 times bisfluoromethyl ether by mol) of trifluoroboron was added. Then, stirring was conducted for 2 hr at 25° C. With this, bisfluoromethyl ether was not detected.

Then, it was washed with 5 g of 10% NaOH aqueous solution and then with 10 g of water, followed by distillation. With this, 18.3 g of fluoromethyl-1,1,1,3,3,3-hexafluoroisopropyl ether having a purity of 99.99% was obtained.

EXAMPLE 4

A 50 ml reaction vessel was charged with 25 g of crude fluoromethyl-1,1,1,3,3,3-hexafluoroisopropyl ether containing 1.3% of bisfluoromethyl ether and 12.3% of a polyether (s) or the like, which had been obtained in EXAMPLE 1. Then, 2.5 g (10%/fluoromethyl-1,1,1,3,3,3-hexafluoroisopropyl ether) of Nation H was added. Then, stirring was conducted for 4 hr at 35° C. With this, bisfluoromethyl ether decreased to 0.001%.

Then, Nation H was filtered out. The flitrate was washed with 5 g of 10% NaOH aqueous solution and then with 10 g of water, followed by distillation. With this, 18.8 g of fluoromethyl-1,1,1,3,3,3-hexafluoroisopropyl ether having a purity of 99.99% was obtained.

According to the method of the present invention, it is possible to obtain fluoromethyl-1,1,1,3,3,3-hexafluoroisopropyl ether that has an extremely high purity and is used as an inhalation anesthetic.

We claim:

1. A method of purifying a crude fluoromethyl-1,1,1,3,3,3-hexafluoroisopropyl ether containing a fluorinated ether by-product, said method comprising the sequential steps of:

(1) treating said crude fluoromethyl-1,1,1,3,3,3,-hexafluoroisopropyl ether with at least one member selected from the group consisting of a Brönsted acid, a Lewis acid and an acid fixed to a resin;

(2) treating a mixture obtained by the step (1) with an alkaline aqueous solution; and (3) distilling fluoromethyl-1,1,1,3,3,3,-hexafluoroisopropyl ether from a mixture obtained by the step (2).

2. A method according to claim 1 wherein said fluorinated ether by-product is bisfluoromethyl ether.

3. A method according to claim 1 wherein a molar ratio of said Brönsted acid or said Lewis acid to said fluorinated ether by-product is from 0.2 to 20.

4. A method according to claim 1 wherein a weight ratio of said acid fixed to resin to said crude fluoromethyl-1,1,1,3,3,3,-hexafluoroisopropyl ether is from 0.01 to 0.5.

5. A method according to claim 1 wherein the step (1) is conducted at a temperature of from 0° to 100° C.

* * * * *